US00PP13189P2

(12) United States Plant Patent
Bentley

(10) Patent No.: US PP13,189 P2
(45) Date of Patent: Nov. 5, 2002

(54) ***GAURA LINDHEIMERI* PLANT NAMED 'CRIMSON BUTTERFLIES'**

(76) Inventor: Howard Bentley, 3 Harris Road, Wonga Park, Victoria (AU)

( * ) Notice: Subject to any disclaimer, the term of this patent is extended or adjusted under 35 U.S.C. 154(b) by 0 days.

(21) Appl. No.: 09/837,406

(22) Filed: Apr. 18, 2001

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database, 2001/06, GTI Retrieval Software, citation for 'Crimson Butterflies'.*

* cited by examiner

*Primary Examiner*—Bruce R. Campell
*Assistant Examiner*—Susan B. McCormick
(74) *Attorney, Agent, or Firm*—Christie, Parker & Hale, LLP

(57) ABSTRACT

Described is a new *Gaura lindheimeri* plant having short, narrow, crimson colored leaves growing on a very compact plant with short racemes.

3 Drawing Sheets

LATIN NAME OF GENUS AND SPECIES

The present invention relates to a new *Gaura lindheimeri* plant.

VARIETY DENOMINATION

The new *G. lindheimeri* plant has the varietal denomination 'Crimson Butterflies'.

BACKGROUND OF THE INVENTION

The new variety *G. lindheimeri* 'Crimson Butterflies' was discovered as a seedling variant of the variety *Gaura lindheimeri* 'Siskiyou Pink' in a controlled planting.

SUMMARY OF THE INVENTION

The new variety of a *G. lindheimeri* plant is an evergreen perennial shrub, which has a compact, dense, spreading, growing habit distinguished by its leaves, flower color and size. Asexual reproduction of the new variety by vegetative cuttings in Wonga Park, Victoria, Australia has demonstrated that the distinguishing characteristics are transferred through succeeding generations.

COMPARISON WITH PARENT

The new variety differs from its parent, 'Siskiyou Pink', in being more compact and dense and having a shorter raceme length. The new variety also has a shorter and more narrow leaf length than its parent variety and has a different leaf color.

BRIEF DESCRIPTION OF ILLUSTRATIONS

The accompanying illustrations depict specimen plants of the new variety in color as true as possible in color photographic illustrations of this nature.

DETAILED DESCRIPTION OF THE NEW VARIETY

Figure 1:
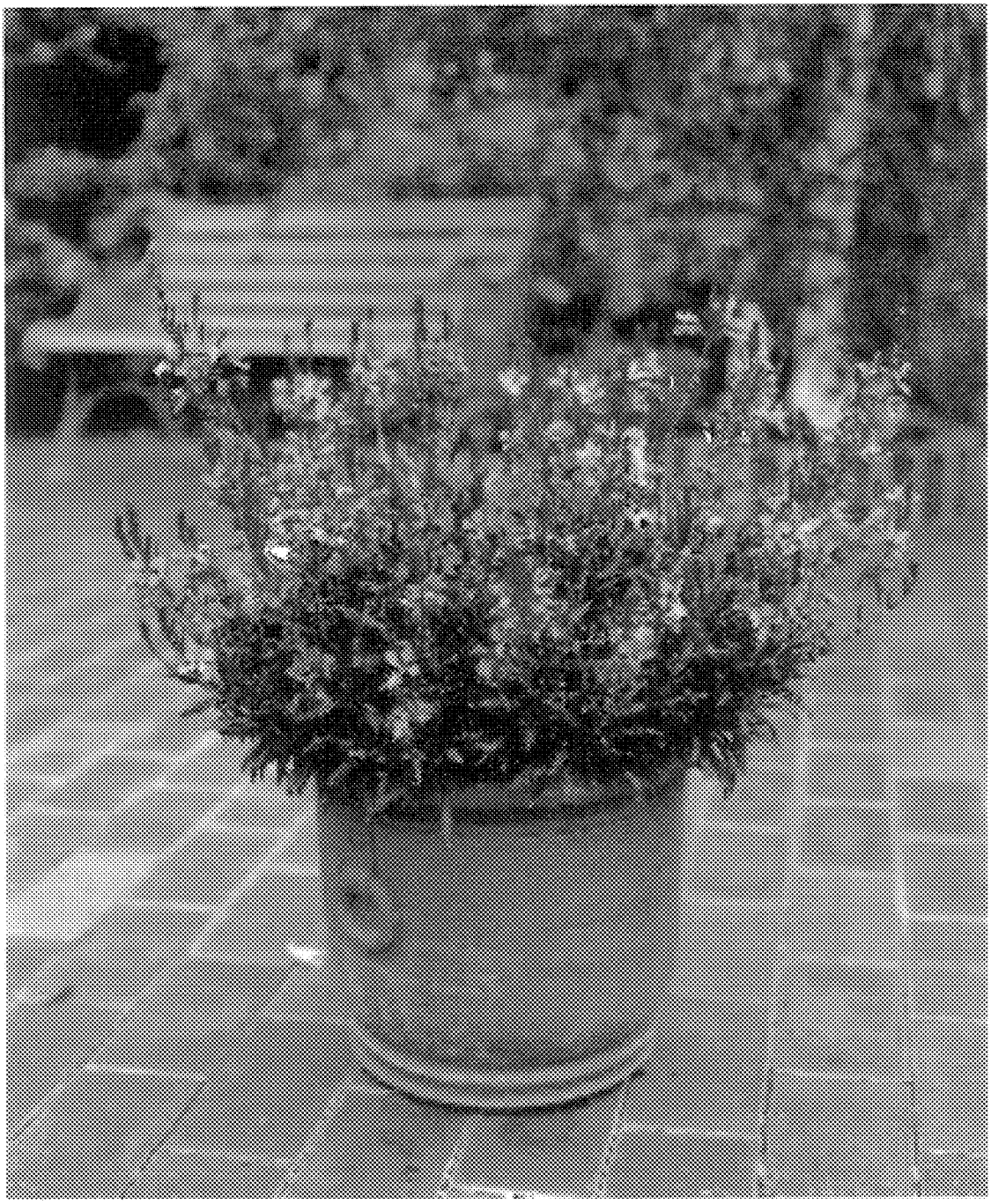
FIG. 1 shows the plant of the new variety.
Figure 2:
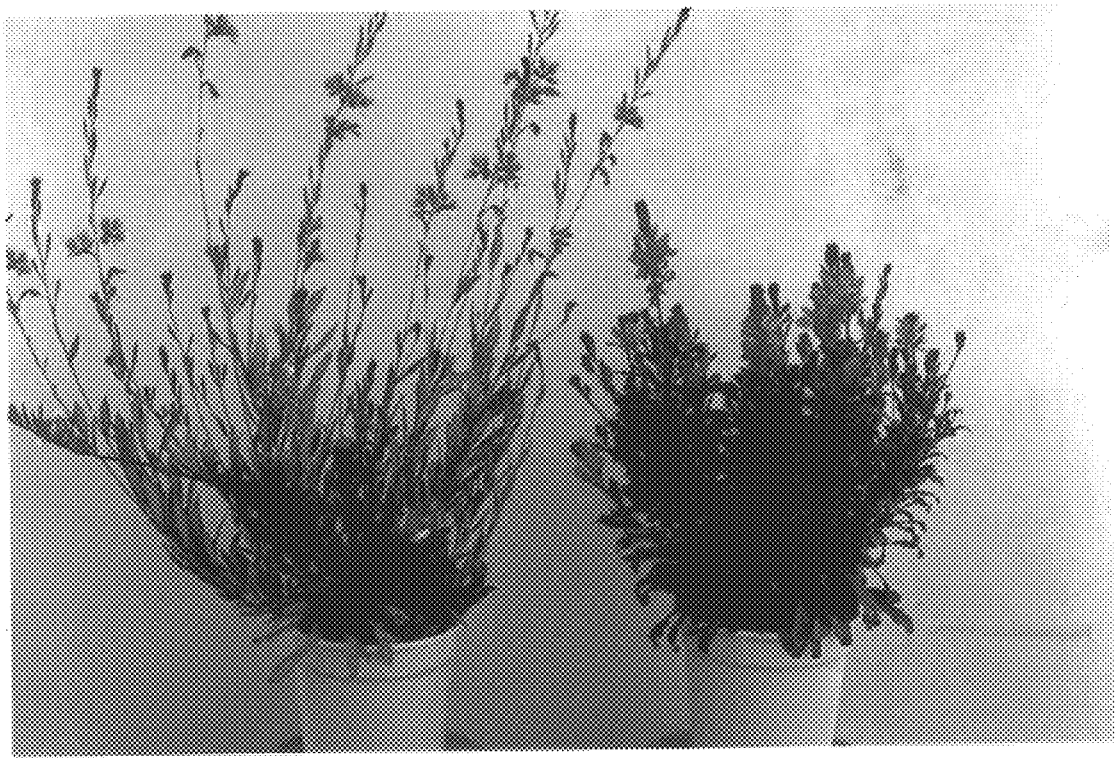
FIG. 2 shows the new variety aside its parent variety.
Figure 3:
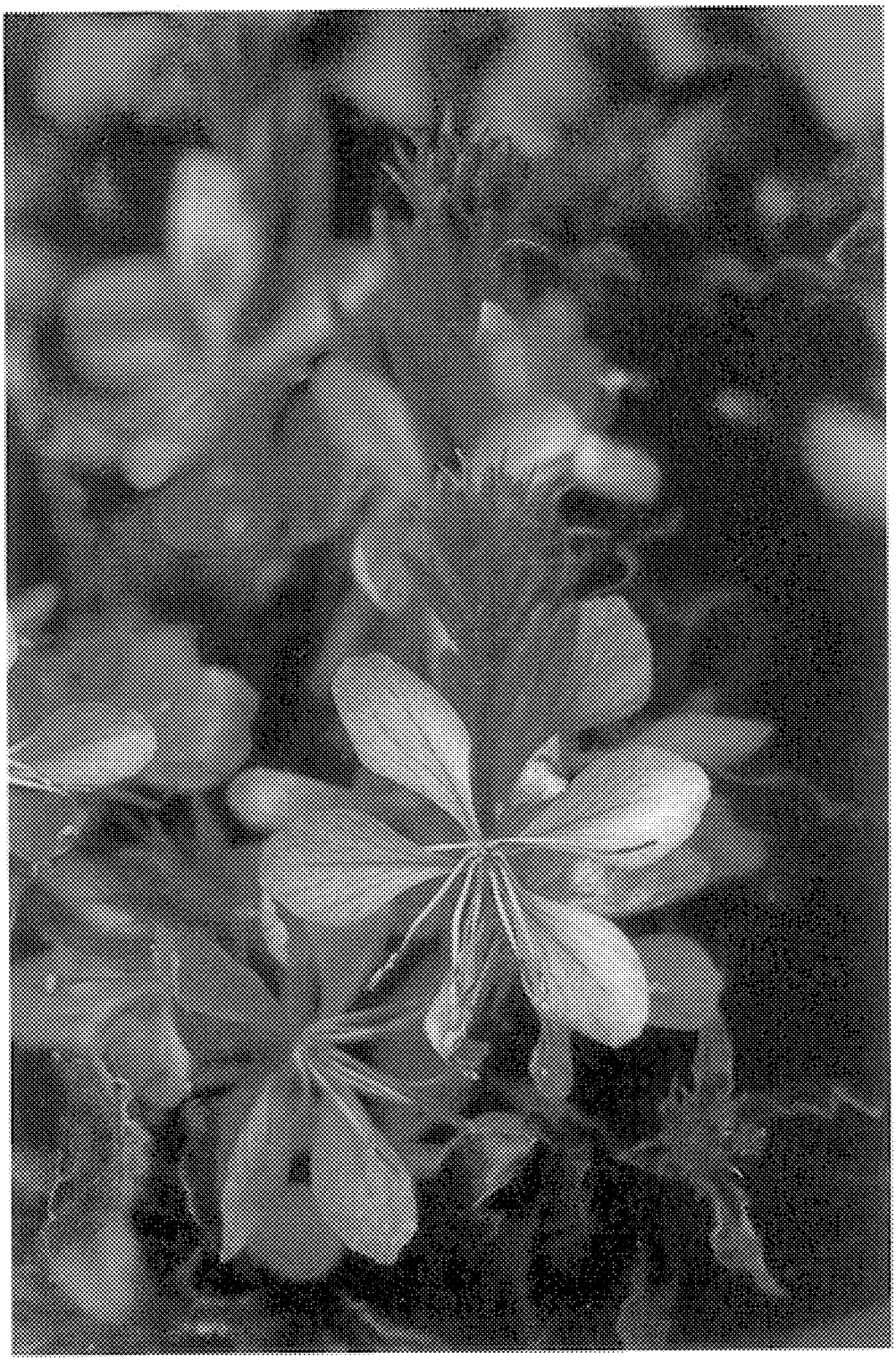
FIG. 3 shows a close up of the flower of the new variety.

The following is a description of the new variety taken from plants grown out-of-doors in Wonga Park, Victoria, Australia during the month of April. Color designations used herein are from *The Royal Horticultural Society Colour Chart* (1995 ed.) ("RHSCC").

PLANT

The plant grows in a spreading habit with compact, dense growth.

Height and width: About 30 cm high by about 60 cm wide, excluding terminal flowering stems, for a mature plant.

Vigor: Over one growing season (9 months), new basal stems will grow to a length about 30 cm excluding terminal flower stems.

ROOT

Root initiation occurs between 10 and 14 days using a suitable rooting hormone and propagation facility.

FOLIAGE

Leaflet:

*Size.*—About 52 mm long and about 11 mm wide.

*Quantity.*—Dense, with a mean of about 7 leaves per 50 mm of stem, measured from the first full sized leaf down the stem.

Color:

*Leaflet base.*—Near 187A.

*Leaflet tips.*—Near 183C.

Shape: Leaves are linear to lanceolate ovate to narrow ovate.

Texture:

*Upper side.*—Smooth with fine pubescence.

*Underside.*—Smooth with fine pubescence.

Veination: Reticulate.

Edge: Slight undulate margins observed.

Petiole: Virtually absent as the leaf blade extends to the stem nodal union.

WOOD

Stem:

*Diameter.*—Mean is about 2 mm (measured at first fully developed leaf).

*Length.*—Mean is about 30 cm (per growing season).

*Color.*—Red/purple, near 59A.

Internode length: Mean is about 16 mm.

Bark: Bark covered with a fine pubescence.

FLOWER

Arrangement: Raceme length very short, with a mean of about 20 cm (measured when last flowers only left); color near 183A; tubular, diameter about 30 to 31 mm; 4 to 5 petals; color near 53D.

Height: About 24.5 mm.

Width: About 34.5 mm.

Number open per raceme: Mean is about 4.

Petal:

*Shape.*—Oblanceolate; margin entire; base attenuate, apex acute to obtuse.

*Size.*—Length mean is about 17 mm; width mean about 10 mm.

*Texture.*—Smooth.

*Color.*—Upper and lower surfaces, near 63B to 63C; veination near 63A.

Sepals: Four fused at tip, mean about 12 mm long; color near 184B when flower opens.

Pedicel: Length mean about 10 mm, diameter mean about 1 mm; color near 183B.

Flowering period: August to April (southern hemisphere, Melbourne, Australia.

Fragrance: None.

WINTER HARDINESS

Winter hardy to between 7° and 5° C.

RESISTANCE TO DISEASE

Good; observed to be generally disease resistant.

BREEDING

First observed as open-pollinated seedling in trial bed among a crop of seedlings raised from the parent variety. This compact variant was isolated in 1997 and has since been propagated asexually through 5 generations to ensure uniformity and stability of the development of 'Crimson Butterflies'.

REPRODUCTIVE ORGANS

Arrangement: Stamens, filaments and anthers are regularly arranged at the base, but bunched in a pendula formation.

Filaments: About 8 per flower; length about 9 mm.

Color: White to pink (dependant on age), near 62D.

Anthers: Length about 3mm; crimson color, near 187A.

Pollen: Yellow.

Styles: Thin, singular, medium length (about 14 mm); color near 186C; 1 style per flower.

Stigma: Color between pale green and cream colored, near 149D; width about 2 mm.

Hips:

*Shape.*—Oval to linear.

*Size.*—Small with no seed protrusion.

Seeds: No seeds observed on plant.

I claim:

1. A new *Gaura lindheimeri* plant of the variety substantially as shown and described.

* * * * *

*GAURA LINDHEIMERI*
'SISKIYOU PINK'
(Comparison/Parent Variety)

*GAURA LINDHEIMERI*
'CRIMSON BUTTERFLIES'
(New Variety)